US005955470A

United States Patent [19]

Gittos

[11] Patent Number: 5,955,470

[45] Date of Patent: Sep. 21, 1999

[54] DERIVATIVES OF AMIDE ANALOGS OF CERTAIN METHANO BRIDGED QUINOLIZINES

[75] Inventor: Maurice W. Gittos, Plobsheim, France

[73] Assignee: Merrell Pharmaceuticals, Inc., Cincinnati, Ohio

[21] Appl. No.: 09/181,888

[22] Filed: Oct. 29, 1998

Related U.S. Application Data

[63] Continuation of application No. 08/589,905, Jan. 23, 1996, abandoned, which is a continuation-in-part of application No. 08/450,038, May 25, 1995, abandoned, which is a continuation of application No. 08/348,001, Dec. 1, 1994, abandoned, which is a continuation of application No. 08/141,438, Oct. 22, 1993, abandoned, which is a continuation of application No. 07/894,311, Jun. 4, 1992, abandoned.

[30] Foreign Application Priority Data

Jun. 11, 1991 [EP] European Pat. Off. ............ 91 401 550

[51] Int. Cl.[6] .......................... A61K 31/44; A61K 31/53; C07D 455/00; C07D 265/36

[52] U.S. Cl. ...................... 514/294; 514/230.5; 514/243; 514/278; 546/18; 546/94; 544/105; 544/183

[58] Field of Search ................................ 514/230.5, 243, 514/278, 294; 546/18, 94; 544/105, 183

[56] References Cited

U.S. PATENT DOCUMENTS

| | | | |
|---|---|---|---|
| 3,951,998 | 4/1976 | Hibino et al. | 260/306.6 |
| 4,879,301 | 11/1989 | Umio et al. | 514/321 |
| 4,906,755 | 3/1990 | Gittos | 546/94 |
| 5,011,846 | 4/1991 | Gittos | 514/294 |
| 5,140,023 | 8/1992 | Becker et al. | 514/214 |
| 5,234,921 | 8/1993 | Flynn et al. | 514/214 |
| 5,280,028 | 1/1994 | Flynn et al. | 514/294 |
| 5,387,586 | 2/1995 | Diouf et al. | 514/233.8 |
| 5,508,287 | 4/1996 | Gittos | 514/294 |

FOREIGN PATENT DOCUMENTS

| | | |
|---|---|---|
| 0330824 | 9/1989 | European Pat. Off. . |
| 0377967 | 7/1990 | European Pat. Off. . |
| 0200444 | 11/1997 | European Pat. Off. . |
| 2193633 | 2/1988 | United Kingdom . |

OTHER PUBLICATIONS

Burger, Alfred; "Medicinal Chemistry" 2d Ed. Inter Science, NY p. 42 (1960).

*Primary Examiner*—Mukund J. Shah
*Assistant Examiner*—Brenda Coleman
*Attorney, Agent, or Firm*—Balaram Gupta

[57] ABSTRACT

This invention relates to novel amide derivatives of certain 2,6-methano-2H-quinolizine-type compounds, to the intermediates and processes for their preparation, to their ability to antagonize the effects of serotonin at the $5HT_3$ receptors, and to their end-use application in the treatment of chemotherapeutically-induced nausea and vomiting, as anti-anxiety agents, in the symptomatic treatment of pain associated with migraine, as anti-arrhythmic agents, in the treatment of cognitive disorders, in treating hallucinatory endogenous psychoses of the type manifested in patients suffering from schizophrenia, and mania, in the treatment of glaucoma, for stimulating gastric motility, to combat drug abuse, to treat sleep apnea and to treat irritable bowel syndrome.

23 Claims, No Drawings

DERIVATIVES OF AMIDE ANALOGS OF CERTAIN METHANO BRIDGED QUINOLIZINES

This is a continuation of application Ser. No. 08/589,905, filed Jan. 23, 1996, now abandoned, which is a continuation-in-part of application Ser. No. 08/450,038, filed May 25, 1995, now abandoned, which is a continuation of application Ser. No. 08/348,001, filed Dec. 1, 1994, now abandoned, which is a continuation of application Ser. No. 08/141,438, filed Oct. 22, 1993, now abandoned, which is a continuation of application Ser. No. 07/894,311, filed Jun. 4, 1992, now abandoned, all of which are herein incorporated by reference.

This invention relates to novel amide derivatives of certain 2,6-methano-2H-quinolizines-type compounds, to the intermediates and processes for their preparation, to their ability to antagonize the effects of serotonin at the $5HT_3$ receptors, and to their end-use application in the treatment of chemotherapeutically-induced nausea and vomiting, as anti-anxiety agents, in the symptomatic treatment of pain associated with migraine, as anti-arrhythmic agents, in the treatment of cognitive disorders, in treating hallucinatory endogenous psychoses of the type manifested in patients suffering from schizophrenia, and mania, in the treatment of glaucoma, for stimulating gastric motility, to combat drug abuse, to treat sleep apnea and to treat irritable bowel syndrome.

More specifically, this invention relates to compounds of the formula (I)

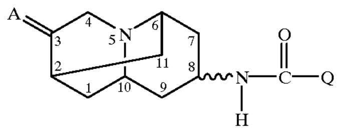

hydrates, tautomers, stereo and geometric isomers, and to the pharmaceutically acceptable acid addition and quaternary ammonium salts thereof, wherein A is $H_2$, O, (H)(OH), $NOR_1$, or

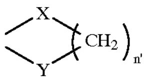

with n being 2 or 3,

X and Y are O or S, each $R_1$ is independently H or $C_{1-4}$ alkyl, $R_2$ is H, halogeno, $C_{1-4}$ alkyl, $C_{1-4}$ alkoxy, $C_3$–$C_6$ cycloalkylmethoxy, OH, —CN or $C(O)NH_2$, Z is O, S or $NR_1$, Q is a heterocyclic or carbocyclic moiety of the formulae (a)

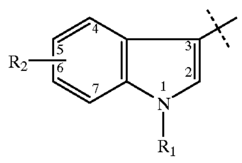

-continued (b)

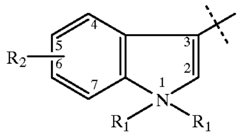

(c)

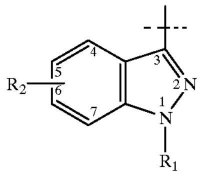

(d)

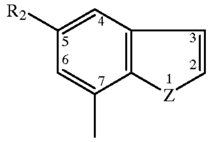

(e)

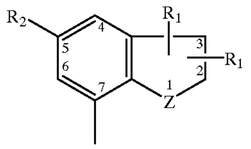

(f)

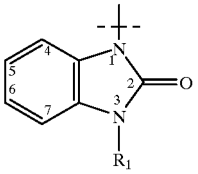

(g)

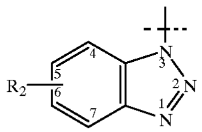

(h)

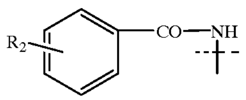

(i)

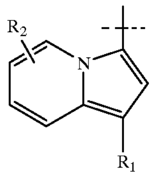

(j)

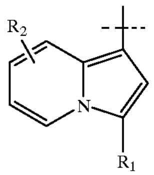

-continued (k)

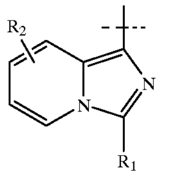

(l)

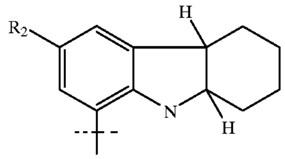

(m)

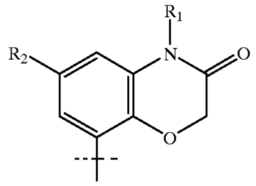

(n)

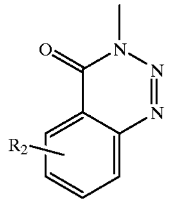

Preferably, the invention relates to the subset of formula I as follows: A compound of the formula (I)

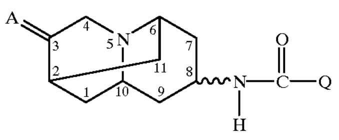

hydrates, tautomers, stereo and geometric isomers,and to the pharmaceutically acceptable acid addition salts thereof, wherein A is $H_2$, O, (H)(OH), or

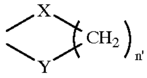

with n being 2 or 3,

X and Y are O or S, each $R_1$ is independently H or $C_{1-4}$ alkyl, $R_2$ is H, halogeno, $C_{1-4}$ alkyl, or $C_{1-4}$ alkoxy, Z is O, S or $NR_1$, Q is a heterocyclic or carbocyclic moiety of the formulae (a)

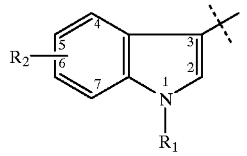

(b)

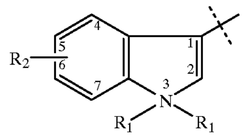

(c)

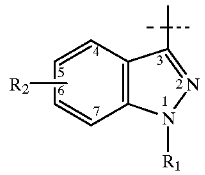

(d)

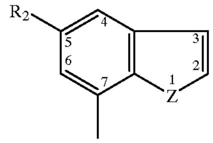

(e)

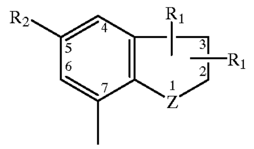

(g)

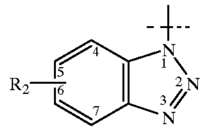

More preferably, Q is (c) and/or (e).

As used herein, the wavy line bonding the nitrogen atom of the ~NHC(O)Q moiety to the 8-position of the octa-hydro-2,6-methano-2H-quinolizin moiety (hereinafter sometimes referred to as the methano bridged quinolizinyl moiety) indicates that the bonding may be in the endo (trans) or the exo (cis) configuration. When the wavy line is modified to a solid line it designates the endo configuration while a dotted line indicates an exo configuration. In those instances wherein A represents =(H)(OH) a chirality exists presenting d- or 1- isomers and racemic mixtures thereof. The hydrates are those compounds wherein A represents =(OH)(OH). In those instances wherein A represents

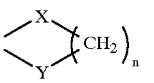

the moiety represents a 5- to 6- membered ring moiety, which, for convenience, may be written $—O(CH_2)_nO—$, $—O(CH_2)_nS—$, $—S(CH_2)_nS—$; the so-indicated terminal bonds of the sulfur and/or oxygen atom being attached to the 3-position carbon atom of the methano bridged quinolizinyl moiety, the $C_{1-4}$ alkyl radicals include the straight and branched-chain saturated lower aliphatic hydrocarbons having 1 to 4 carbon atoms such as, for example, methyl, ethyl, propyl, isopropyl, n-butyl, and isobutyl; the $C_{1-4}$ alkoxy radicals are the ether analogs thereof, such as, for example, methoxy and ethoxy. Halogeno includes fluoro, chloro or bromo. Except when otherwise indicated the $R_2$ substituents attached to the depicted moieties may be attached to any of the carbon atoms of the moiety through which the $R_2$— bond is depicted. Again for convenience and to avoid any ambiguity, it is to be noted that the valence bond traversing the dotted line is the bond through which the depicted cyclic Q moities of sub-formulae (a) through (m) are attached to the carbon atom of the amide function at the 8-position of the methano bridged quinolizinyl moiety. The $R_1$ substituents on the Q=(e) moiety may be at the 3,2; 3,3; or 2,2 positions. Preferably, $R_1$ substituents are at the 3,3 position. The (e) moiety may also have a double bond between positions 2 and 3 with $R_1$ substituents at appropriate available positions.

Exemplary of the preferred Q heterocycles of sub-formulae (a) to (m) are such moieties as (a) N-$R_1$-$R_2$ substituted-1H-indole, (b) $R_2$-substituted-3$R_1$, 3$R_1$-2,3-dihydro-1H indoles, (c) $R_2$-substituted-N-$R_1$-1H-indazoles, (d) $R_2$-substituted-benzofurans and $R_2$-substituted-benzo [b] thiophenes, (e) 5-$R_2$-3$R_1$, 3$R_1$-2,3-dihydro-benzothiophenes and 5-$R_2$-3$R_1$, 3$R_1$-2,3-dihydro-benzofurans, (f) N-$R_1$-2,3-dihydro-2-oxo-1H-benzimidazoles, and (g) $R_2$ substituted-1H-benzotriazoles.

The pharmaceutically acceptable acid addition salts referred to above can be non-toxic salts with suitable acids such as those with inorganic acids, for example, hydrochloric, hydrobromic, nitric, sulfuric or phosphoric acids; or with organic acids such as organic carboxylic acids, for example, acetic, propionic, glycolic, maleic, hydroxymaleic, malic, tartaric, citric, salicylic, 2-acetyloxybenzoic, nicotinic or isonicotinic; or organic sulfonic acids, for example, methanesulfonic, ethanesulfonic, 2-hydroxyethanesulfonic, 4-toluenesulfonic or 2-naphthalenesulfonic. Quaternary ammonium salts are formed with alkyl halides such as methyl chloride, methyl bromide, methyl iodide or ethyl bromide; or with sulfate esters such as methyl 4-toluenesulfonate or methyl 2-naphthalenesulfonate.

In general, the compounds of this invention may be prepared using processes and techniques analogously known in the art. In essence, the compounds of the present invention (1) can be prepared by reacting a di-amine or a reactive derivative thereof, said di-amine having the formula (6)

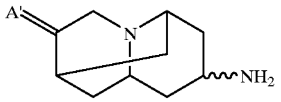

wherein A' is $=H_2$ or —X—$(CH_2)_2$—Y or —X—$(CH_2)_3$—Y with X and Y being O or S; with a reactive equivalent of an acid of the formula

QCOOH wherein Q is defined as above. By a reactive equivalent of the acid is meant the corresponding acid chloride or bromide, the trichloromethyl ester, a mixed anhydride or the carboxylic acid imidazole obtained by the reaction of the appropriate acid halide with N,N-carbonyl diimidazole or any similar acid derivative which would yield the simple carboxylic acid amide on reaction with a primary amine.

The di-amines (6) used as a reactant in the above procedure can be obtained by a multistep procedure from hexahydro-8-hydroxy-2,6-methano-2H-quinolizin-3(4H) one (2) whose synthesis was described in U.S. Pat. No. 4,906,755, incorporated herein by reference. Specifically in the case of the di-amine wherein A' is —$O(CH_2)_2O$— or —$O(CH_2)_3O$— the 3,(4H)one is protected as an ethylene or propylene glycol by reaction with ethylene glycol or 1,3-propanediol in the presence of a suitable acid such as p-toluenesulfonic acid in a hydrocarbon solvent such as benzene or toluene using a Dean and Stark apparatus to remove the water. The 8-hydroxy group is then oxidized to a keto group [to produce compounds (4)] by the use of oxalyl chloride and dimethyl sulfoxide following the procedure of Swern and the 8-keto group is transformed into an oxime (compounds 5) by reaction with hydroxylamine hydrochloride. Reduction of the oximino group with a tetrahydrofuran solution of aluminium hydride (generated from lithium aluminium hydride and concentrated sulfuric acid) affords the required di-amine reactant (6) in which the 8-amino group is in the endo (trans) configuration. Reduction of the oximino group by nascent hydrogen generated by dissolving sodium in amyl alcohol affords the di-amine reactant in which the 8-amino group adopts the exo (cis) configuration.

Similarly by using 2-hydroxyethane thiol or 3-hydroxypropanethiol in the place of ethylene glycol or 1,3-propanediol the above procedure yields the epimeric di-amine wherein A' is —$O(CH_2)_2S$— and —$O(CH_2)_3S$— respectively. By using ethylene 1,2-dithiol or propylene-1,3-dithiol in the place of ethylene glycol or 1,3-propanediol the above procedure affords the epimeric di-amine reactants wherein A' is —$S(CH_2)_2S$— and —$S(CH_2)_3S$—. These dithianes can be reduced to the epimeric di-amine reactants wherein A' is $=H_2$ by the use of hydrazine and Raney nickel in a lower alkanol solvent such as 2-propanol at an elevated temperature (60°–100° C.).

Various procedures can be used to convert those amides (7) of the invention wherein A' is —$X(CH_2)_2Y$— or —$X(CH_2)_3Y$—, X and Y are O or S; to other bridged derivatives of the present invention by standard methods. Thus, the dithioketal, i.e. wherein A' is —$S(CH_2)_2S$— or —$S(CH_2)_3S$— can be reduced with hydrazine in the presence of Raney nickel as described above to give the amides of the present invention wherein A" is $H_2$. The ketals, i.e. wherein A' is —$O(CH_2)_2O$— or —$O(CH_2)_3O$—, can be transformed into those compounds wherein A" is =O by aqueous acid hydrolysis using, for example, 2M HCl at temperatures from 40° to 100° C. The 1,3-oxathiolanes i.e. wherein A' is —$O(CH_2)_2S$— or —$O(CH_2)_3S$— can be transformed into the amides wherein A" is =O by reaction with mercuric chloride in aqueous acetonitrile or a lower alcohol at temperatures from 10°–40° C. The keto group can be further transformed into an alcohol (9) group by reduction with an alkali metal borohydride in a lower alcohol, and into compounds in which A'" is a hydroximino (=NOH) or an alkoxyimino (=$NOR_1$) group by reaction with the hydrochlorides of hydroxylamine or O-alkylhydroxylamines respectively. The products from some of these transformations are mixtures of stereo or geometric isomers and these can be separated into their pure isomers by standard methods.

Of course, in those instances wherein the heterocycles moiety of QCOOH contains a primary or secondary amine, it is preferably protected during the above reactions, preferably utilizing a benzyl group when the amine is a secondary amine, and a benzyloxycarbonyl group to protect a primary amine. In either case the protecting group in the product is removed by conventional procedures, e.g., by hydrogenation with $H_2$ with palladium as a catalyst. Similarly when $R_2$ functions would interfere with the reactions required for forming the desired product, such moieties may also be protected and then de-protected according to standard techniques and processes well-known in the art.

These reactions may be generically depicted by the following Reaction Scheme.

REACTION SCHEME A

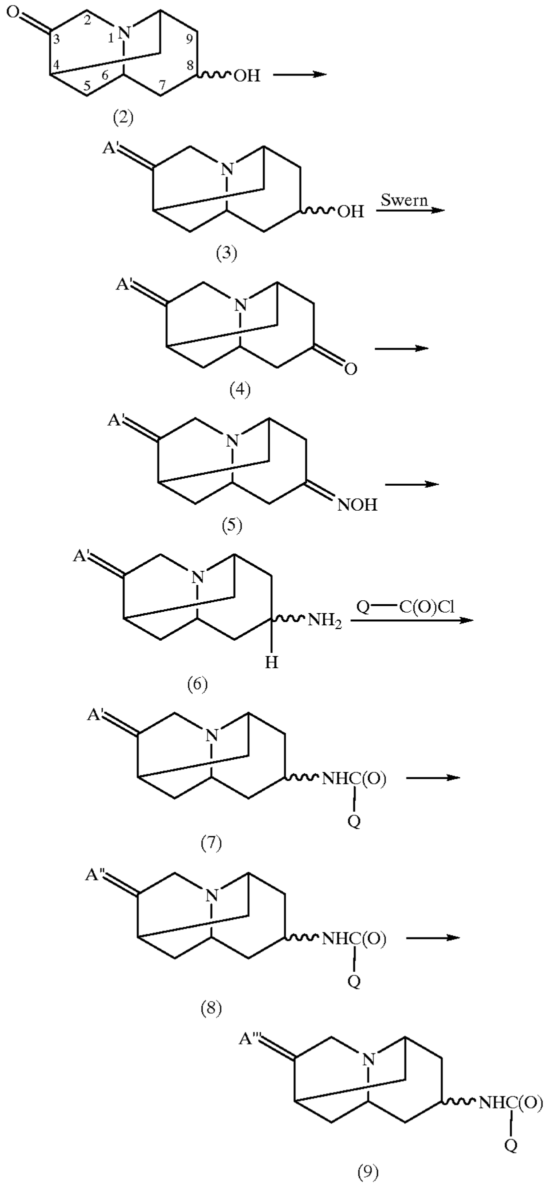

wherein A' is $=H_2$, $—X—(CH_2)_2—Y$ or $—X—(CH_2)_3—Y$, X and Y being as previously defined as is Q, and A" is O or $H_2$, and A'" is =(OH)(H), $=NOR_1$, or =(OH)(OH).

EXAMPLE 1

Intermediate

Trans-octahydrospiro-[(1,3)-dioxolane-2,3'-(2,6)-methano-2'H-quinolizin]-8'-ol

A solution of trans hexahydro-8-hydroxy-2,6-methano-2H-quinolizin-3(4H)-one hydrochloride (10.88 g, 0.05 mol) in a minimum of water was strongly basified by the addition of a saturated aqueous solution of potassium carbonate and the free base isolated by extraction with tetrahydrofuran evaporation of the dried magnesium sulfate extract gave 9.05 g of the free base. A solution of the free base (9.05 g) in benzene (200 ml) was treated with ethylene glycol (3.41 g, 1.1 equiv.) and methanesulfonic acid (5.81 g, 1.2 equiv.) and the stirred mixture refluxed for 2 hours using a Dean and Stark trap. The cream solid was filtered off, dissolved in a minimum of water, and the solution strongly basified by the addition of an excess of a saturated potassium carbonate solution. Extraction with tetrahydrofuran and evaporation of the dried magnesium sulfate extract afforded the titled compound (10.69 g, 95% )

EXAMPLE 2

Intermediate

Octahydrospiro-[(1,3)-dioxolane-2,3'-(2,6)-methano-2'H-quinolizin]-8'-one

A solution of dimethylsulfoxide (3.58 g, 1.2 equiv.) in methylene chloride (20 ml) was slowly added to a stirred solution of oxalylchloride (5.33 g, 1.1 equiv.) in methylene chloride (100 ml) at −70° C. under nitrogen. The mixture was stirred for a further 10 minutes after the addition and then treated with a suspension of trans-octa-hydrospiro-[(1,3)-dioxolane-2,3'-(2,6)-methano-2'H-quinolizin]-8'-ol (8.59 g, 1 equiv.) in methylene chloride (100 ml). After stirring at −70° C. for 15 minutes triethylamine (26.5 ml, 5 equiv.) was slowly added and the stirred mixture allowed to return to room temperature overnight. Water (30 ml) and a saturated aqueous solution of potassium carbonate (10 ml) were added, the separated organic phase dried over magnesium sulfate and evaporated to give an orange brown sticky solid contaminated with some dimethyl sulfoxide. The solid was redissolved in ethyl acetate, the solution charcoaled and evaporated to give the title compound as an orange brown solid (7.06 g, 83%).

EXAMPLE 3

Intermediate

Octahydrospiro-[(1,3)-dioxolane-2,3'-(2,6)-methano-2'H-quinolizin]-8'-one oxime

A solution of octahydrospiro-[(1,3)-dioxolane-2,3'-(2,6)-methano-2'H-quinolizin]-8'-one (4.45 g, 0.02 mol) in water (100 ml) was stirred with a solution of hydroxylamine hydrochloride (1.66 g, 0.024 mol) in water (20 ml) for 2 hours, during which time a precipitate formed. The mixture was concentrated, basified by the addition of a saturated aqueous solution of potassium bicarbonate and extracted with tetrahydrofuran. Some of the solid remained insoluble and was filtered off (0.85 g). The dried organic extracts were evaporated and the combined solid was recrystallized from a mixture of ethanol and methanol to give the title compound (3.6 g, 76%).

EXAMPLE 4

Intermediate

Trans-octahydrospiro-[(1,3)-dioxolane-2,3'-(2,6)-methano-2'H-quinolizin]-8'-amine A solution of concentrated sulfuric acid (4.04 g, 0.041 mol) in anhydrous tetrahydrofuran was slowly added to a stirred suspension of lithium aluminium hydride (3.17 g, 0.083 mol) in tetrahydrofuran at −10° C. under nitrogen. The mixture was stirred for 2 hours and the temperature allowed to rise to room temperature. Finally powdered octahydrospiro-[(1,3)-dioxolane-2,3'-(2,6)-methano-2'H-quinolizin]-8'-one oxime (4.97 g, 0.021 mol) was added followed by anhydrous tetrahydrofuran (70 ml) and the stirred mixture heated at 40° C. for 3 hours. After leaving overnight at room temperature the stirred mixture was cooled to 10° C. and treated with a solution of water (7 ml) in tetrahydrofuran (7 ml). The mixture was stirred at 30° C. for one hour, filtered and the precipitate washed with tetrahydrofuran. The dried filtrate magnesium sulfate was evaporated to give the title compound as a white crystalline solid (3.56 g). The grey precipitate was strongly basified with aqueous potassium hydroxide and the mixture extracted with tetrahydrofuran by decantation. Evaporation of the dried extract gave a further 0.58 g of the white solid. Total yield was 4.14 g (88% yield).

EXAMPLE 5

Intermediate

Indazole-3-carboxylic acid

A solution of concentrated sulfuric acid (19.1 g, 0.19 mol) in water (200 ml) prepared in a 2 litre beaker was cooled to 0° C. Isatin (14.7 g, 0.1 mol) was added to a solution of sodium hydroxide (4.1 g, 0.105 mol) in water(65 ml) at 50° C. and the dark red solution cooled to 0° C. A solution of sodium nitrite (6.9 g, 0.1 mol) in water (235 ml) at 0° C. was added and the mixture added to the rapidly stirred solution of sulfuric acid during 5 minutes. The temperature was not allowed to rise above 4° C. (controlled by the addition of ice). The yellow brown foamy mixture was stirred for a further 15 minutes before being treated with a solution of stannous chloride hydrate (54 g, 0.24 mol) in concentrated hydrochloric acid (85 ml) at 0° C. The mixture was stirred for one hour and the crude product filtered. The material was recrystallized as follows: about half of the solid was placed in a 1 litre flask and ~500 ml of water was added. The solution was heated on a hot-plate until boiling and was then filtered hot to give a dark yellow-brown precipitate and an orange-yellow solution. The solution was left to cool overnight. The recrystallizing solution was filtered to give a yellow solid and a pale yellow filtrate. The solid was put in the oven to dry. The process was repeated with the other half of the crude product and the two mother liquors were pooled together as were the solid products. The dark yellow-brown substance filtered off during recrystallization was boiled with 150 ml of water, filtered and the resulting solution was left to recrystallize. It was then treated as above. The pooled mother liquors were concentrated to ⅓ volume and the solution allowed to crystallize. The solid thus obtained was added to the rest. On drying, 7.27 g solid yellow powder product was obtained, with an m.p. 263–264° C.

EXAMPLE 6

Intermediate

Methyl-1-methylindazole-3-carboxylate

A mixture of indazole-3-carboxylic acid (5.67 g, 0.035 mol) methyl iodide (10.43 g, 0.073 mol), potassium carbonate (10.16 g, 0.073 mol) and dimethyl formamide (100 ml) was stirred at 50° C. overnight. The orange solution was filtered, evaporated and the residue dissolved in a mixture of ethyl acetate and water. The ethyl acetate phase was separated, dried and evaporated to give a red brown oil (6.63 g) consisting mainly of a mixture of methyl 1- and 2-methylindazole carboxylates. They were separated using flash chromatography on silica gel (eluant hexane-ethyl acetate 70-30) to give methyl 1-methylindazole-3-carboxylate (3.12 g) as a yellow solid (47%) and methyl 2-methyl-indazole-3-carboxylate (1.62 g, 24%) as a yellow oil which slowly crystallized.

EXAMPLE 7

Intermediate

1-Methylindazole-3-carboxylic acid

Methyl-1-methylindazole-3-carboxylate (3.1 g, 0.016 mol) was stirred with a solution of sodium hydroxide (0.78 g, 0.02 mol) in tetrahydrofuran (100 ml) for 2 hours at room temperature, the solution evaporated and the yellow residue were dissolved in water. Acidification with methanesulfonic acid precipitated 1-methylindazole-3-carboxylic acid (2.19 g). A further crop (0.3 g) was obtained by extraction of the aqueous acid solution with a mixture of ether and methylene chloride. Total yield 2.49 g (87%).

EXAMPLE 8

Intermediate

1-Methyl-indazole-3-carbonyl chloride

A stirred suspension of 1-methyl-indazole-3-carboxylic acid (0.68 g, 3.86 mol) in anhydrous ether (50 ml) was treated with thionyl chloride (0.28 ml, 3.84 mol) and a few drops of dimethylformamide. After stirring for one hour the solid dissolved. The solvent was evaporated to give 1-methyl-indazole-3-carbonyl chloride as a yellow solid (0.75 g, 100%).

EXAMPLE 9

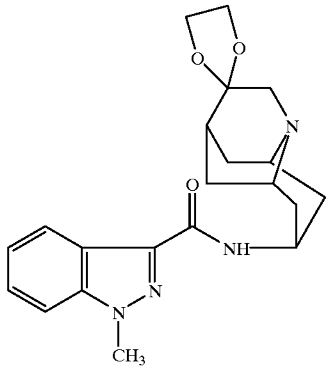

Trans-octahydro-[(1', 3')-dioxolane-2', 3"-(2', 6')-methano-2"H-quinolizin]-8"-yl-1-methyl-1H-indazole-3-carboxamide A stirred mixture of 1-methyl-1H-indazole-3-carbonyl chloride (0.747 g, 3.84 mmol), trans-octahydrospiro [(1,3)-dioxolane-2,3'-(2,6)-methano-2'H-quinolizin]-8'-amine (0.86 g, 3.84 mmol) and acetonitrile (25 ml) was refluxed for 2 hours. Lithium carbide (0.11 g, 1 equiv.) was added, as a base, and the stirred mixture refluxed for a further 3 hours.

The solvent was evaporated, the brown solid residue suspended in water and the mixture treated with aqueous potassium carbonate solution. The brown oil was extracted with ethyl acetate, the extracts washed with water, and then evaporated to give a yellow oil (1.04 g, 71%) which crystallized. The solid was recrystallized from ethyl acetate to give the pure indazole carboxamide.

EXAMPLE 10

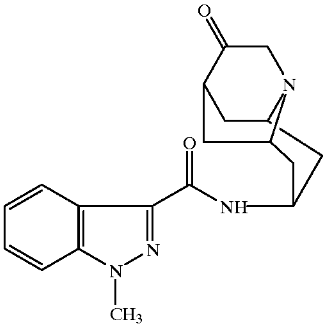

Trans-1-methyl-N-(octahydro-3-oxo-2,6-methano-2H-quinolizin-8-yl)-1H-indazole-3-carboxamide methane sulfonate A stirred solution of trans-octahydro-[(1', 3')-dioxolane-2', 3''-(2', 6')-methano-2''H-quinolizin]-8''-yl-1-methyl-1H-indazole-3-carboxamide (0.97 g, 2.54 mmol) in 1N HCl was refluxed for 4 hours and stirred at room temperature overnight during which time a precipitate formed. The mixture was basified by the addition of potassium carbonate solution and the product isolated by extraction with ethyl acetate. Evaporation of the dried ethyl acetate extracts gave a solid (0.56 g) which was dissolved in a solution of methane sulfonic acid (0.16 g) in water (20 ml). Evaporation of the filtered solution gave a solid which was recrystallized from isopropanol to give the title compound as a half hydrate.

EXAMPLE 11

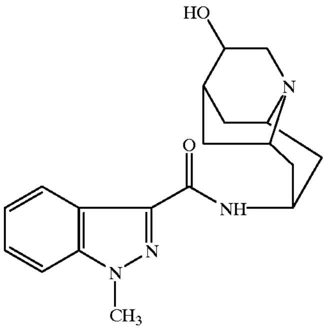

Trans-1-methyl-N-(octahydro-3-hydroxy-2,6-methano-2H-quinolizin-8-yl)-1H-indazole-3-carboxamide methane sulfonate A solution of trans-1-methyl-N-(octahydro-3-oxo-2,6-methano-2H-quinolizin-8-yl)-1H-indazole-3-carboxamide methane sulfonate (252 mg, 0.58 mmol) in a minimum of water was basified with aqueous potassium carbonate and the base (191 mg) isolated by extraction with ethyl acetate. Sodium borohydride (107 mg, 5 equiv.) was added to a solution of the base in ethanol (5 ml) and the mixture stirred at room temperature overnight. Methane sulfonic acid (250 mg) was added, the solution evaporated, and the residue dissolved in a minimum of water. Basification with aqueous potassium carbonate and extraction with ethyl acetate gave the title compound as the free base (165 mg). It was dissolved in a mixture of methanesulfonic acid (47 mg) and water (1 ml), the solution evaporated and the oil recrystallized from isopropanol to give the title compound which may be separated with the optical isomers of 10-camphor sulfonic acid to obtain enantiomers.

EXAMPLE 12

Intermediate

Trans-octahydrospiro-[1,3-thioxolane-2,3'-(2,6)-methano-2'H-quinolizin]-8'-ol

A stirred mixture of trans-hexahydro-8-hydroxy-2,6-methano-2H-quinolizin-3(4H)-one (9.8 g), methane sulfonic acid (5.88 g), 2-mercapto ethanol (4.35 g) and benzene (200 ml) was refluxed for 2 hours using a Dean and Stark trap. During this time water (1.4 ml) was collected. The solid was filtered from the cooled solution, dissolved in water and the solution basified with saturated aqueous potassium carbonate. Extraction with a mixture of ethyl acetate tetrahydrofuran (1:1) and evaporation of the dried extract gave crystals of the titled compound m.p. 194° C. (10.4 g).

"Thioxolane" as used herein and hereafter is meant to define the moiety (a) wherein X is oxygen, Y is sulfur and n is 2.

EXAMPLE 13

Intermediate

Octahydrospiro-[1,3-thioxolane-2,3'-(2,6)-methano-2'H-quinolizin]-8'-one

A solution of dimethyl sulphoxide (4.07 g) in methylene chloride (20 ml) was slowly added to a stirred solution of oxalyl chloride (6.06 g) in methylene chloride (100 ml) at −70° C. under nitrogen. The mixture was stirred for a further 10 minutes and then treated with a suspension of trans-octahydrospiro-[1,3-thioxolane-2,3'-(2,6)-methano-2'H-quinolizin]-8'-ol (10.47 g) in methylene chloride (100 ml). After stirring at −70° C. for 15 minutes, triethylamine (30.2 ml) was slowly added and the stirred mixture allowed to return to room temperature overnight. Water (30 ml) and a saturated aqueous solution of potassium carbonate (10 ml) were added and the separated organic phase dried over a mixture of magnesium sulfate and animal charcoal. The residue on evaporation of the solvent was chromatographed on silica gel using a mixture of ethyl acetate and ethanol (4:1) as eluant to give the pure titled compound.

EXAMPLE 14

Intermediate

Octahydrospiro-[(1,3)-thioxolane-2,3'-(2,6)-methano-2'H-quinolizin]-8'-one-oxime A solution of octahydrospiro-[(1,3)-thioxolane-2,3'-(2,6)-methano-2'H-quinolizin]-8'-one (4.5 g) in water (100 ml) was stirred with a solution of hydroxylamine hydrochloride (1.56 g) in water (20 ml) for 1 night at room temperature. The mixture was concentrated, basified by the addition of saturated aqueous potassium bicarbonate and the product extracted with tetrahydrofuran. Some of the solid remained insoluble and was filtered off. The dried organic extracts were evaporated and the combined solid was recrystallized from a mixture of ethanol and methanol to give the titled compound (4.52 g).

EXAMPLE 15

Intermediate

Trans-octahydrospiro-[(1,3)-thioxolane-2,3'-(2,6)-methano-2'H-quinolizin]-8'-amine A solution of concentrated sulfuric acid (3.50 g) in anhydrous tetrahydrofuran was slowly added to a stirred suspension of lithium aluminium hydride (2.72 g) in tetrahydrofuran at −10° C. under nitrogen. The mixture was stirred for 2 hours and the temperature allowed to rise to room temperature. Finally powdered octahydrospiro-[(1,3)-thioxolane-2,3'-(2,6)-methano-2'H-quinolizin]-8'-one oxime (4.52 g) was added followed by anhydrous tetrahydrofuran (70 ml) and the stirred mixture heated at 40° C. for 3 hours. After leaving overnight at room temperature the stirred mixture was cooled to 10° C. and treated with a solution of water (7 ml) in tetrahydrofuran (7 ml). The mixture was stirred at 30° C. for one hour, filtered and the precipitate washed with tetrahydrofuran. The dried filtrate magnesium sulfate was evaporated to give the title compound as a white crystalline solid (3.56 g). The grey precipitate was strongly basified with aqueous potassium hydroxide and the mixture extracted with tetrahydrofuran by decantation. Evaporation of the dried extract gave a further 0.58 g of the white solid. Total yield was 3.74 g (88% yield).

EXAMPLE 16

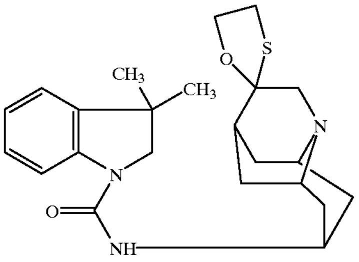

Trans-octahydro-[(1,3)-thioxolane-2,3'-(2,6)-methano-2'H-quinolizin]-8"-yl-2,3-dihydro-3,3-dimethyl-1H-indole-1-carboxamide A solution of 2,3-dihydro-3,3-dimethyl-1H-indole (2 g) and triethylamine (1.4 g) in methylene chloride (10 ml) was added to a stirred solution of trichloromethyl chloroformate (1.64 ml) in methylene chloride at 0° C. The mixture was allowed to stir overnight at room temperature and then washed successively with water (10 ml) and 2N HCl. Evaporation of the dried organic phase gave an oil (2.58 g).

A stirred mixture of the above oil (0.64 g) and trans-octahydrospiro-[(1,3)-thioxolane-2,3'-(2,6)-methano-2'H-quinolizin]-8'-amine (0.5 g) in toluene (25 ml) was refluxed overnight and cooled to room temperature. The solid (0.76 g) was filtered off, partitioned between tetrahydrofuran and saturated aqueous potassium carbonate and the organic phase separated and dried. Evaporation of the organic solvent afforded a solid residue which was purified by silica gel chromatography using methylene chloride methanol (8:2) as eluant, to give the titled compound as a crystalline solid m.p. 107–108° C.

EXAMPLE 17

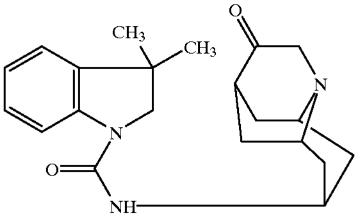

Trans-2,3-Dihydro-3,3-dimethyl-N-(octahydro-3-oxo-2,6-methano-2H-quinolizin-8-yl)1H-indole-1-carboxamide ethane dioate hydrate A mixture of trans-octahydro-[(1,3)-thioxolane-2,3'-(2,6)-methano-2'H-quinolizin]-8"-yl-2,3-dihydro-3,3-dimethyl-1H-indole-1-carboxamide (0.33 g), calcium carbonate (0.12 g) mercuric chloride (0.33 g), acetonitrile (16 ml) and water (4 ml) was vigorously stirred at room temperature for two days. The solid was filtered off, washed three times with ethyl acetate and the combined filtrate and washings partitioned between water and a mixture of ethyl acetate-tetrahydrofuran (1:1). The dried organic phase was evaporated and the residue chromatographed on silica gel using firstly ethyl acetate-methanol (4:1) and then methylene chloride-methanol (9:1) as eluants. The base recovered from the second eluant was treated with ethanolic oxalic acid (1 equivalent) to give crystals of the titled compound.

EXAMPLE 18

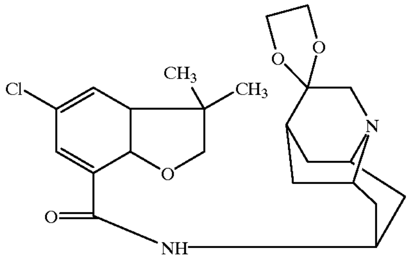

Trans-5-chloro-2,3-dihydro-2,2-dimethyl-N-[octahydrospiro-(1,3-dioxolane-2,3'-(2,6)-methano-2'H-quinolizin)-8'-yl]-7-benzofurancarboxamide hydrochloride A stirred mixture of octahydrospiro-[(1,3)-dioxolane-2,3'(2,6)-methano-2'H-quinolizin]-8'-ol (3.6 g), 5-chloro-2,3-dihydro-2,2-dimethylbenzofuran-7-carboxylic acid chloride (4 g) and toluene (70 ml) was refluxed overnight. After cooling the titled compound was filtered off (6.61 g).

Following the same procedure 2-chloro-5a,6,7,8,9,9a-hexahydrodibenzofuran-4-carboxylic acid chloride is reacted with octahydrospiro-[(1,3)-dioxolane-2,3'-(2,6)-methano-2'H-quinolizin]-8'-ol to give trans-2-chloro-5a,6,7,8,9,9a-hexahydro-N[octahydrospiro(1,3-dioxolane-2,3'-(2,6)-methano-2'H-quinolizin)-8'-yl]-4-dibenzofurancarboxamide hydrochloride.

EXAMPLE 19

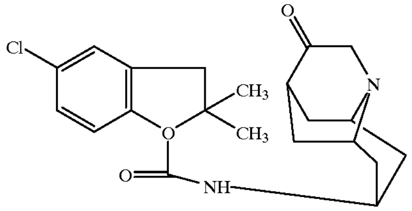

Trans-5-chloro-2,3-dihydro-2,2-dimethyl-N-[octahydro-3-oxo-2,6-methano-2H-quinolizin)-8-yl]-7-benzofurancarboxamide A stirred solution of trans-5-chloro-2,3-dihydro-2,2-dimethyl-N-[octahydrospiro(1,3-dioxolane-2,3'-(2,6)-methano-2'H-quinolizin)-8'-yl]-7-benzofurancarboxamide hydrochloride (19 g) in 2N HCl (200 ml) was refluxed overnight and allowed to cool. The crystals were filtered off and dried to give the titled compound as its hydrochloride. An aqueous solution of the salt was basified by the addition of saturated aqueous potassium carbonate and the base obtained by extraction with ethyl acetate tetrahydrofuran (1:1) and evaporation of the dried solvent.

Following the same procedure trans-2-chloro-5a,6,7,8,-9,9a-hexahydro-N-[octahydrospiro-(1,3-dioxolane-2,3'-(2,6)-methano-2'H-quinolizin)-8'-yl]-4-benzofurancarboxamide hydrochloride is hydrolysed to give trans-2-chloro-5a,6,7,8,9,9a-hexahydro-N(octahydro-3-oxo-2,6-methano-2H-quinolizin-8-yl)-4-dibenzofurancarboxamide.

EXAMPLE 20

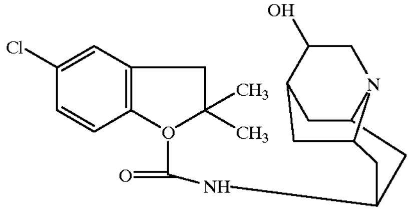

Trans-5-chloro-2,3-dihydro-2,2-dimethyl-N-[octahydro-(3-hydroxy-2,6-methano-2H-quinolizin)-8-yl)-7-benzofurancarboxamide methanesulfonate A mixture of trans-5-chloro-2,3-dihydro-2,2-dimethyl-N-(octahydro-3-oxo-2,6-methano-2H-quinolizin-8-yl)-7-benzofurancarboxamide (0.35 g), sodium borohydride (0.17 g) and ethanol (15 ml) was stirred overnight at room temperature and the ethanol then evaporated off. A solution of the residue in water was acidified to a pH of 1 by the addition of 2N HCl and the acidic solution basified by the addition of saturated aqueous potassium carbonate. Extraction with ethyl acetate tetrahydrofuran (1:1) and evaporation of the dried extract gave a base which was treated with ethanolic methane sulphonic acid (1 equivalent) to give the titled compound separated with tartaric acid to obtain enantiomers.

Similarly trans-2-chloro-5a,6,7,8,9,9a-hexahydro-N-(octahydro-3-oxo-2,6-methano-2H-quinolizin-8-yl)-4-dibenzofurancarboxamide is transformed into trans-2-chloro-5a,6,7,8,9,9a-hexahydro-N (octahydro-3-hydroxy-2,6-methano-2H-quinolizin-8-yl)-4-dibenzofurancarboxamide methanesulfonate.

EXAMPLE 21

Intermediate

Trichloromethyl-1-benzotriazolecarboxylate

A stirred mixture of benzotriazole (3 g), triphosgene (11.22 g), charcoal (1 g) and anhydrous toluene was refluxed overnight and filtered. Evaporation of the filtrate gave an oily solid which was suspended in a mixture of hexane and ether (1:1). Filtration and evaporation of the filtrate gave the titled compound as an oil.

EXAMPLE 22

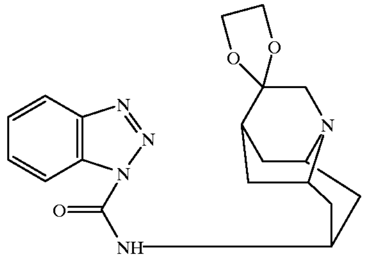

Trans-N-[octahydrospiro(1,3-thioxolane-2,3'-(2,6)-methano-2'H-quinolizin)-8'-yl]-1-benzotriazolecarboxamide A stirred mixture of trichloromethyl-1-benzotriazolecarboxylate (0.5 g), trans-octahydrospiro-[(1,3)-thioxolane-2,3'-(2,6)-methano-2'H-quinolizin]-8-amine (0.43 g) and toluene (30 ml) was refluxed for 2 hours and cooled. Ether was added and the solid filtered off. A solution of the solid in water was extracted with ethyl acetate and then basified with saturated aqueous potassium carbonate. The mixture was extracted with tetrahydrofuran and the concentrated organic phase chromatographed over silica gel using a mixture of ethyl acetate/methanol (9:1) to give the titled compound as a white solid m.p. 152° C. (0.3 g).

EXAMPLE 23

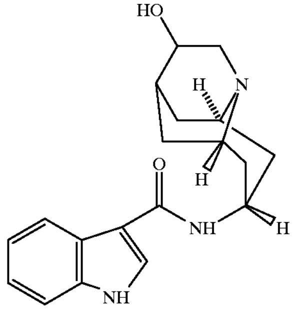

Trans-N-(octahydro-3-hydroxy-2,6-methano-2H-quinolizin-8-yl)-1H-indole-3-carboxamide methane sulfonate A stirred mixture of 1H-indole-3-carbonyl chloride (0.718 g, 4 mmol), trans-octahydrospiro[(1,3)-dioxolane-2,3'-(2,6)-methano-2H-quinolizin]-8'-amine (0.896 g, 4 mmol) and acetonitrile (25 ml) was refluxed for 2 hours. Lithium carbide (0.115 g, 4 mmol) was added as a base and the stirred mixture refluxed for a further 3 hours. The solvent was evaporated, the residue suspended in water and the mixture treated with an excess of an aqueous solution of potassium carbonate. The oil was extracted with ethyl acetate, the extracts washed with water and then evaporated to give a yellowish oil (1 g).

A stirred solution of the above yellowish oil (1 g) in 1N HCl was refluxed for four hours. The cooled mixture was basified by the addition of potassium carbonate solution and the product isolated by extraction with ethyl acetate. Evaporation of the dried ethyl acetate extracts gave a solid (0.5 g.).

A solution of the above solid (0.26 g) in ethanol (20 ml) was treated with sodium borohydride (0.152 g) and the mixture stirred at room temperature overnight. Methanesulfonic acid (250 mg) was added, the solution evaporated and the residue dissolved in a minimum of water. Basification with aqueous potassium carbonate and extraction with ethyl acetate/tetrahydrofuran (1/1) gave the title compound as the free base (170 mg). It was dissolved in a mixture of methanesulfonic acid (50.5 mg) and water (1 ml), the solution evaporated and the residue recrystallized from isopropanol to give trans-N-(octahydro-3-hydroxy-2,6-methano-2H-quinolizin-8-yl)-1H-indole-3-carboxamide methanesulfonate.

EXAMPLE 24

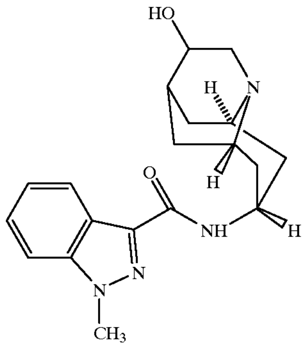

(−)-Trans-1-methyl-N-(octahydro-3-hydroxy-2,6-methano-2H-quinolizin-8-yl)-1H-indazole-3-carboxamide methanesulfonate Continuing from the synthesis described in Example 11 herein, a solution of trans-1-methyl-N-(octahydro-3-hydroxy-2,6-methano-2H-quinolizin-8-yl)-1H-indazole-3-carboxamide (free base), 11.8 g, 34 mmol) in acetonitrile (200 ml) was treated with (−)-camphor-10-sulfonic acid (7.9 g, 34 mmol). After leaving overnight the (−)(−) salt was filtered off and recrystallized four times from acetonitrile to give 6.12 g of the pure salt. An aqueous solution of the salt was basified with potassium carbonate solution and the base extracted into tetrahydrofuran. Addition of an equivalent of methanesulfonic acid and evaporation to dryness gave (−)-trans-1-methyl-N-(octahydro-3-hydroxy-2,6-methano-2H-quinolizin-8-yl)-1H-indazole-3-carboxamide methanesulfonate. α-D=3.64.

The corresponding (+) enantiomer was obtained using (+)-camphosulfonic acid.

The compounds of the present invention block or antagonize the M receptors for 5-hydroxytryptamine (5HT) on afferent sensory neurons otherwise known at $5HT_3$ receptors. The activity of the compounds against 5HT can be assessed by determining their $pA_2$ values in the isolated rabbit heart as described by J. R. Fozard et al., Eur. J. Pharmacol. 59, 195–210 (1979). The activity of these compounds against 5HT in vivo can be assessed by measurement of the effect of the compound on the Von Bezold-Jarisch reflex induced by 5HT injected intravenously into the rat [see Paintal A. S., Physiol. Rev. 53, 159–227 (1973); J. R. Fozard, Naunyn-Schmiedeberg's Arch. Pharmacol. 326, 36–44 (1984)].

The compounds of this invention may be utilized for their $5HT_3$ receptor blocking properties in the treatment of the disease states herein disclosed within the dose range of 0.01 to 10 mg per kilogram of body weight with the preferred compounds being effective within the dose range of 0.01 to 0.1 mg per kilogram of body weight, parenterally, or 0.25 to 1 mg per kilogram of body weight given enterally. The following examples illustrate some methods for testing conditions responsive to treatment with the compounds of the present invention by blocking the $5\text{-}HT_3$ receptor. Other methods of testing for conditions not illustrated but disclosed herein are well known to those skilled in the art.

As used in this application:

(a) the phrase "gastric motility", refers to the rate at which the stomach empties its contents into the duodenum.

(b) the term "glaucoma" refers to a group of eye diseases characterized by an increase in intraocular pressure, which can cause pathological changes in the optic disk and typically defects in the field of vision.

(c) the term "intraocular pressure" refers to the pressure within the eyeball.

(d) the term "anxiety" refers to a condition where a patient is experiencing fear, apprehension, uncertainty, etc., and can be accompanied with physical manifestations such as, tachycardia, tremors, sweating, etc.

(e) the term "psychosis" refers to a condition where the patient, e.g., a human, experiences a major mental disorder of organic and/or emotional origin characterized by derangement of the personality and loss of contact with reality, often with delusions, hallucinations or illusions, such as, for example, schizophrenia or mania.

(f) the term "treatment" refers to the ability to either relieve or alleviate the patient's disease or condition.

(g) the term "condition" means an abnormal state such as in a disease state which normally requires treatment.

(h) the term patient refers to mammals such as human beings.

The compounds of Formula I exhibit the pharmacological action increasing the motility of the upper gastrointestinal tract. This means that the compounds increase the rate at which the stomach empties its contents into the duodenum.

Thus, the compounds are useful in the treatment of gastric stasis. Gastric stasis refers to a condition where the stomach's ability to empty its contents into theduodenum is impaired. This typically produces discomfort in the patient.

The compounds are also useful in the treatment of gastroesophageal reflux. Gastroesophageal reflux refers to a condition, where small quantities of gastric juice are refluxed into the lower part of the esophagus. The acid gastric juice irritates the mucosa of the esophagus causing pain and discomfort in the patient.

The quantity of compound required to produce this gastric motility stimulating effect described above will vary with the particular compound utilized, the patient, the route of administration, the severity of the patient's condition, the presence of other underlying disease states in the patient, and other medications which are being administered concurrently to the patient. Generally though, a patient will respond to dosage range of from 0.01 to 10 mg/kg/day.

One method of demonstrating that the compounds of Formula I increase gastric motility is the following test protocol. Male mice should be fasted overnight prior to being utilized in the test. One group of mice should be administered saline intraperitoneally, and the other group should be administered a compound of Formula I such as at a dose of 5 mg/kg intraperitoneally in a saline carrier.

One hour after administration of either the drug or a saline control, the mice should be given 0.3 ml intragastrically of a suspension containing 10% w/v charcoal, and 5% w/v tragacanth gum with the aid of a feeding needle. Fifteen minutes later the animals should be sacrified.

The stomachs should be surgically removed and the weighed. The contents should be washed from the stomach, and then the stomachs should be reweighed. The groups should then be compared utilizing the change in weight of the stomach after washing, as an indicator of the rate of gastric emptying.

As noted above, the compounds are also useful as antipsychotics. The quantity of compound required to produce this antipsychotic therapeutic effect will vary with the particular compound utilized, the patient, the severity of the patients illness, the presence of other disease states within the patient, and the mode of administration. Generally though, a patient's psychosis will respond to the compound at a dosage range at from about 0.01 mg/kg to about 10 mg/kg of patient body weight per dosage.

The compounds of Formula I are not dopamine receptor antagonists. Therefore, patients being administered one of these compounds will not experience the numerous side effects that are typically associated with the neuroleptic agents that are currently available, such as chlorpromazine, haloperidol, fluphenazine, etc.

One manner of demonstrating the antipsychotic utility of these compounds is by their ability to block the hyperactivity which usually accompanies the intra-accumbens administration of amphetamine in rats. The following test protocol can be utilized to demonstrate this activity.

This pharmacological effect is measured indirectly. This is accomplished by measuring what effect the compound has upon the ability of a rat to avoid an electrical shock, which it has previously learned to avoid. Initially, the rat should be placed in a test chamber capable of delivering an electrical shock to the rat at a specified rate, for example once every 20 seconds. The test chamber should also be capable of delaying the rate at which electrical shocks are administered if the rat performs the proper avoidance behavior, such as moving from one side of the chamber to the other. The rat should be repeatedly exposed to this test chamber on a regular basis until it has learned to consistently engage in the behavior which delays the response. After it has learned this behavior it is suitable for further testing. A bilateral cannulae should be implanted in the nucleus accumbens according to the following procedure. The rat should be anesthetized and mounted in a stereotactic device. A small hole is drilled through the skull at coordinates A 1.5, L 1.4[1] (relative to bregma) [[1] Paximo G. and Watson L., "The Rat Brain in Stereotactic Coordinates", 2nd Ed., m Academic Press, 1986.], bilaterally and an additional hole is drilled near by for a small machine screw. A 20 gauge cannulae is placed stereotactically, so as to terminate 1 mm above, the nucleus (V 6.0, brain surface)[1]. Dental acrylic can be utilized to secure the cannulae to the anchor screw and a 25 gauge stylus can be utilized as a plug for each cannulae.

At least seven days after surgery, the rat should be exposed to the electrical stimuli in the test chamber in order to ascertain that it can still engage in the behavior which delays the rate at which shocks are administered. Rats demonstrating this avoidance response are suitable for use in the comparative tests.

The rat should be administered intra-accumbens amphetamine (10 mcg/side), subjected to electrical shock in the test chamber and its rate of avoidance recorded.

Thereafter, the rat can be administered the test compound (0.25 ng/side) via the intra-accumbens cannulae. Thirty minutes after administration of the test compound, the rat should be administered intra-accumbens amphetamine (10 mcg/side), subjected to electrical shock in the test chamber and its rate of avoidance recorder.

Rats administered amphetamine alone will exhibit an increased rate of avoidance. Rats administered both amphetamine and a compound of Formula (I) will not exhibit this increased rate avoidance.

The compounds of the present invention exhibit the pharmacological activity of lowering intraocular pressures. Thus, these compounds are useful in the treatment of glaucoma.

The compounds can be administered via ophthalmic dosage forms such as, for example, ophthalmic drops, ophthalmic ointments, and ophthalmic disks. The ophthalmic drops of the present invention should contain from 0.1–10% w/w of one of the compounds of Formula (I). Typically, it will be dissolved in a buffered, isotonic solution containing antimicrobial preservative agents. The ophthalmic ointments will also generally contain from 0.1–10% w/w of one of the compounds of Formula (I) admixed with a suitable base, such as white petrolatum and mineral oil, along with antimicrobial preservatives. The ophthalmic disks will typically be constructed so as to contain a core of active ingredient surrounded by a polymer matrix such as, for example, a hydrophobic ethylene/vinyl acetate copolymer. Specific methods of compounding these dosage forms, as well as appropriate ophthalmic pharmaceutical carriers are known in the art. See Remington's Pharmaceutical Sciences, 16th Ed. Mack Publishing Company, Easton, Pa. (1980).

Typically, the ophthalmic drops or ophthalmic ointments will be administered from 1 to 4 times daily. The ophthalmic disks will be administered weekly.

If desired, the compounds of Formula (I) can be administered systematically in order to lower intraocular pressures. The quantity of compound required to produce this ocular hypotensive effect as the result of systemic administration will vary with the particular compound utilized, the patient, the route of administration, the severity of the patient's glaucoma, the presence of other underlying disease states in the patient, and other medications which are being administered concurrently to the patient. Generally though, a patient's glaucoma will respond to dosage range of from 0.01 to 10 mg/kg/day, if administered systematically.

The compounds of Formula (I) are useful in the treatment of anxiety; that is relieving or alleviating the apprehension, fear, or uncertainty, etc., that patients suffering from anxiety commonly experience, as well as relieving or alleviating the physiological changes associated with anxiety such as tachycardia, tremors, sweating, etc.

The compounds of Formula (I) possess a significant advantage over the anxiolytic agents which are currently available to clinicians, such as chlordiazepoxide, diazepam and other benzodiazepines. The benzodiazepines commonly cause sedation and impairment of motor skills at the dosage levels commonly used in the treatment of anxiety.

The compounds of Formula (I) do not suffer from this disadvantage. They exhibit a wide range at which they demonstrate anxiolytic activity, without causing either sedation or impairment of motor skills.

The quantity of compound required to produce the anxiolytic effect described above will vary with the particular compound utilized, the patient, the route of administration, the severity of the patient's anxiety, the presence of other underlying disease states in the patient, and other medications which are being administered concurrently to the patient. Generally though, a patient's anxiety will respond to dosage range of from 0.01 to 10 mg/kg/day.

The novel compounds of Formula (I) are further useful for the treatment of pain, especially migraine, vascular and cluster headaches and trigeminal neuralgia. They are also useful in the treatment of nausea and vomiting arising from treatment with chemotherapeutic agents, particularly in chemotherapeutic treatment of cancer. The compounds of Formula (I) are also useful in combatting drug-abuse.

In the past, acute attacks of migraine have been treated with a peripheral vasoconstrictor, such as ergotamine, which may be co-administered with caffeine, and dihydroergotamine; an antipyretic analgesic, such as acetylsalicyclic acid or p-acetylaminophenol; and/or an antiemetic such as cyclizine, and thiethylperazine. It has also been reported (J. B. Hughes, Med. J. Aust. 2, No. 17, 580 (1977)] that immediate relief of an acute migraine attack can be obtained by slow intravenous injection of metoclopramide (10 mg).

It is believed that 5-hydroxytryptamine (5-HT) or serotonin is the naturally accuring substance most likely to play a role in the pathophysiology of migraine. Increased amounts of 5-HT and its metabolite 5-hydroxyindoleacetic acid are excreted in the urine during most attacks. Further, plasma and platelet 5-HT concentrations fall rapidly at the onset of an attack and remain low while the headache persists. Moreover, attacks of migraine have been clearly associated with periods of thrombocytopaenia in certain patients. It has been proposed that compounds which block the activity of 5-HT would be of use in the symptomatic treatment of migraine (J. R. Fozard, International Headache Congress 1980, reported in Advances in Neurology, Vol. 33., Raven Press, New York, 1982).

The known migraine prophylactic drugs, methysergide, propanolol, amitriptyline, and chlorpromazine have widely different pharmacological activities but all are 5-HT D-receptor antagonists at the doses used clinically for the prophylaxis of migraine. Metoclopramide is a $5\text{-HT}_3$ receptor antagonist and it has been proposed (J. R. Fozard supra) that a blockade of the $5\text{-HT}_3$ receptor present on afferent sensory neurones affords symptomatic relief in an acute migraine attack.

The potency as 5-HT receptor antagonists of (−) cocaine and some related compounds, including pseudotropyl benzoate (i.e., benzoylpseudotropine) and 3,5-dichlorobenzoyltropine has been reported (J. R. Fozard et al., Eur. J. Pharmacol., 59, (1979) 195–210; J. R. Fozard, Naunyn-Schmiedeberg's Arch Pharmacol., 326, (1984), 36–44. The pA2 values reported for metoclopramide, pseudotropyl benzoate, nor (−) cocaine and benzoyltropine are 7.2, 7.0, 7.7 and 7.2 respectively whilst the $pA_2$ value determined for 3,5-dichlorobenzoyltropine by the same procedure is 9.3 (J. R. Fozard et al., Eur. J. Pharmacol., 49, (1978) 109–112; J. R. Fozard, Naunyn-Schmiedeberg's Arch Pharmacol., 326, (1984), 36–44. In a double-bind clinical trial, 3,5-dichlorobenzoyltropine proved an effective treatment for the acute migraine attack (C. Loisy et al., Cephalalgia, 5, (1985) 79–82. A further series of tropine esters, with $pA_2$ values for blockade of the 5-HT M-receptors between 7.7 and 13.6 have been described by Richardson et al., Nature, 316, (1985) 26–131.

In addition, compounds blocking $5\text{-HT}_3$ receptors, including metoclopramide, 3,5-dichlorobenzoyltropine and (3α-tropanyl)-1H-indole-3-carboxylic acid ester, are highly effective in preventing the nausea and vomiting induced by cancer chemotherapeutic agents in an animal experimental model [W. D. Miner et al., Brit. J. Pharmacol., 88, (1986) 374P; W. D. Miner and G. J. Sanger, Brit. J. Pharmacol., 88, (1986) 497–499; B. Costall et al., Neuropharmacology, 25, (1986) 959–961]. It is believed that cytotoxic drug-induced vomiting involves a 5-HT receptor mechanism [W. D. Miner and G. J. Sanger, Brit. J. Pharmacol., 88, (1986) 497–499]. Accordingly, the compounds of Formula (I) are useful in the treatment of cytotoxic drug-induced vomiting when administered in amounts sufficient to effectively block the said $5\text{-HT}_3$ receptors.

The dosage range at which the compounds of Formula (I) exhibit their anti-migraine ad anti-emetic effects will vary depending upon the particular compound utilized, the patient, the route of administration, the severity of the patient's condition, the presence of other underlying disease states in the patient, and other medications which are being administered concurrently to the patient. Generally though, a patient's condition will respond to a dosage range of from 0.01 to 10 mg/kg/day.

The compounds of Formula (I) exhibit the pharmacological action in treating sleep apnea. Sleep apnea refers to a condition of transient attacks of failure of automatic control of respiration, resulting in alveolar hypoventilation, which becomes more pronounced during sleep.

One method of demonstrating that the compounds of Formula (1) treat sleep apnea is to induce apnea in Wistar rats by i.v. bolus injection of 5-HT or 5-HT agonists and then administer an i.v. injection of the compounds of the present invention. Respiratory parameters and phrenic nerve activity can be monitored. One such procedure is described in the Journal of Pharmacology and Experimental Therapeutics 260(2): 917–924 (1991), incorporated herein by reference.

The dosage range at which compounds of Formula (I) exhibit their effect in the treatment of sleep apnea will vary depending upon the particular compound utilized, the patient, the route of administration, the severity of the patients' condition, the presence of other underlying disease states in the patient, and other medications which are being administered concurrently to the patient. Generally though, a patients' condition will respond to a dosage range of from 0.01 to 10 mg/kg/day.

The compounds of Formula (I) exhibit pharmacological activity in treating irritable bowel syndrome. Irritable bowel syndrome is believed to be the consequence of altered colonic motility. Patients complain of constipation or diarrhea and pain. It is believed that $5\text{-HT}_3$ antagonist may be used to treat irritable bowel syndrome [Gut 31: A1174 (1990); Gastroenterology 98: A394 (1990); Gastroenterology 100: A468 (1991); Gut 32: A1228 (1991)].

The dosage range at which the compounds of Formula (I) exhibit their ability to treat irritable bowel syndrome may vary with the compound used, the patients' condition, the route of administration, etc. Generally though, a patients' condition will respond to a dosage range of from 0.01 to 10 mg/kg/day.

The compounds of Formula (I) can be administered in various manners to achieve the desired effect. The compounds are typically administered either orally or parenterally (subcutaneously, intravenously, intramuscularly). They can also be administered by suppository. As noted above, ophthalmic preparations may also be utilized when glaucoma is being treated.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula (I) can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweeting agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The present compounds can be administered in various manners to achieve the desired effect. The compounds can be administered alone or in the form of pharmaceutical preparations to the patient being treated either orally or parenterally, for example, subcutaneously or intravenously. They can also be administered by inhalation or by suppository. The amount of compound administered will vary and can be any effective migraine-relieving amount or amount effective in cytotoxic drug vomiting. Depending upon the patient and the mode of administration, the quantity of compound administered may vary over a wide range to provide from about 0.01 mg/kg to about 10 mg/kg, usually 0.03 to 3.0 mg/kg, of body weight of the patient per dose. Unit doses of these compounds can contain, for example, from about 0.5 mg to 100 mg, usually 1 to 50 mg and preferably 3 to 30 mg, of the compound and may be administered, for example, from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

Specific formulations of the present invention are prepared in a manner well known per se in the pharmaceutical art and usually comprise one or more active compounds of the invention in admixture or otherwise in association with a pharmaceutically acceptable carrier therefor. The active ingredient will usually be mixed with a carrier, or diluted by a diluent, or enclosed or encapsulated in a capsule, sachet, cachet, paper or other container. A carrier or diluent may be solid, semisolid or liquid material which serves as a vehicle, excipient or medium for the active ingredient. Suitable carriers or diluents are well known per se. See Remington's Pharmaceutical Sciences, Mack Publishing Company, Easton, Pa., for a description of the preparation of such formulations which is hereby incorporated by reference.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is race controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

Thus, in summary, the compounds by virtue of their action of blocking $5HT_3$ receptors have the end-use applications in the treatment of chemotherapeutically induced nausea and vomiting, as anti-anxiety agents, in the treatment of pain associated with migraine, vascular and cluster headaches and trigeminal neuralgia, in the treatment of arrhythmia, in the treatment of cognitive disorders, psychosis e.g. schizophrenia and for combatting drug abuse, glaucoma, in stimulating gastric motility, to treat sleep apnea and to treat irritable bowel syndrome.

As is generally true for large classes of chemical compounds found to be useful as chemotherapeutic agents, certain sub-classes and certain specific compounds are preferred over others. In the instant application those compounds wherein A represents $=H_2$, $=O$ or (H)(OH) are preferred, those wherein n is 2 or 3 are preferred, those wherein X and Y are both oxygen or both are sulfur are preferred, those wherein $R_1$ is H, methyl or ethyl are preferred, those wherein $R_2$ is H, chloro, bromo, methyl, ethyl, methoxy, OH are preferred, and those wherein Q is a member of the sub-formulae (a), (b) and (c) are preferred. Besides the compounds exemplified herein, specifically preferred compounds are:

(Z-trans)-1-methyl-N-(octahydro-3-hydroxyimino-2,6-methano-2H-quinolizin-8-yl)-1H-indazole-3-carboxamide, monomethanesulfonate, trans-2,3-dihydro-3,3-dimethyl-N-[octahydrospiro[(1,3)-dioxolane-2,3'-(2,6)-methano-2'H-quinolizin]-8'-yl]-indole-1-carboxamide, monohydrochloride, 1-methyl-N-(octahydro-3-oxo-2,6-methano-2H-quinolizin-8-yl)-1H-indazole-3-carboxamide, methanesulfonate, hemihydrate, (E-trans)-1-methyl-N-(octahydro-3-hydroxyimino-2,6-methano-2H-quinolizin-8-yl)-1H-indazole-3-carboxamide, trans-N-(octahydro-3-hydroxy-2,6-methano-2H-quinolizin-8-yl)-1H-indole-3-carboxamide, monomethanesulfonate, cis-1-methyl-N-(octahydro-3-oxo-2,6-methano-2H-quinolizin-8-yl)-1H-indazole-3-carboxamide, monomethanesulfonate, and cis-1-methyl-N-(octahydro-3-hydroxy-2,6-methano-2H-quinolizin-8-yl)-1H-indazole-3-carboxamide, monomethanesulfonate.

What is claimed is:

1. A compound of the formula (I)

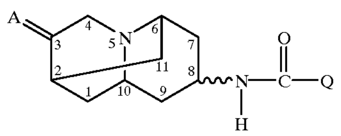

hydrates, tautomers, stereo and geometric isomers, or the pharmaceutically acceptable acid addition or quaternary ammonium salts thereof, wherein A is $H_2$, O, (H)(OH), $NOR_1$, or

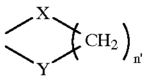

with n being 2 or 3,

X and Y are O or S, each $R_1$ is independently H or $C_{1-4}$ alkyl, $R_2$ is H, halogeno, $C_{1-4}$ alkyl, $C_{1-4}$ alkoxy, $C_3$–$C_6$ cycloalkylmethoxy, OH, —CN or $C(O)NH_2$, Z is O, S or $NR_1$, Q is a heterocyclic or carbocyclic moiety of the formulae (a)

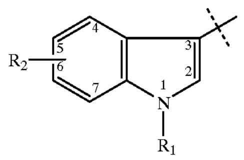

(b)

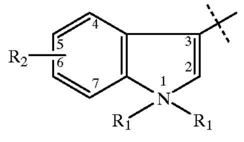

(c)

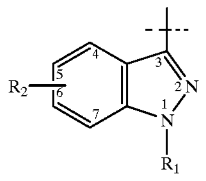

-continued (d)

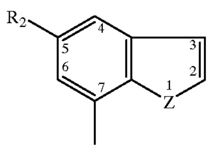

(e)

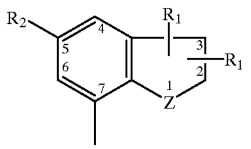

(f)

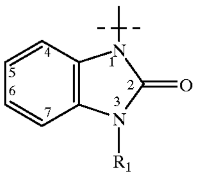

(g)

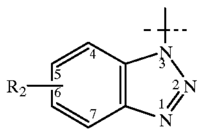

(h)

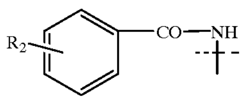

(i)

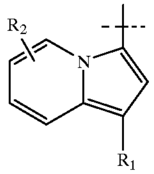

(j)

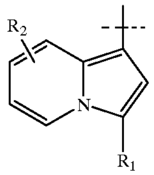

(k)

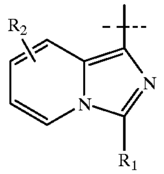

(l)

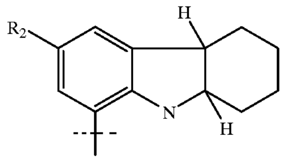

-continued (m)

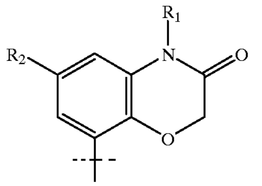

(n)

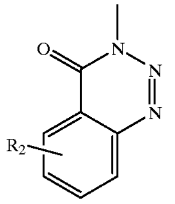

2. The compound of claim 1 wherein A is $H_2$, O, (H)(OH) or

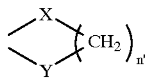

$R_2$ is H, halogeno, $C_{1-4}$alkyl or $C_{1-4}$alkoxy and Q is (a), (b), (c), (d), (e) or (g).

3. The compound of claim 2 wherein Q is (c) or (e).

4. The compound of claim 2 wherein $R_2$ is $C_{1-4}$alkyl.

5. The compound of claim 1 wherein Q is (e).

6. The compound of claim 1 wherein Q is (c).

7. The compound of claim 1 wherein A is O.

8. The compound of claim 1 wherein $R_2$ is halogen.

9. The compound of claim 1 wherein the compound is trans-octahydro-[(1', 3')-dioxolane-2', 3"-(2', 6')-methano-2"H-quinolizin]-8"-yl-1-methyl-1H-indazole-3-carboxamide or a pharmaceutically acceptable salt thereof.

10. The compound of claim 1 wherein the compound is trans-1-methyl-N(octahydro-3-oxo-2,6-methano-2H-quinolizin-8-yl)-1H-indazole-3-carboxamide or a pharmaceutically acceptable salt thereof.

11. The compound of claim 1 wherein the compound is trans-1-methyl-N-(octahydro-3-hydroxy-2,6-methano-2H-quinolizin-8-yl)-1H-indazole-3-carboxamide or a pharmaceutically acceptable salt thereof.

12. The compound of claim 1 wherein the compound is trans-octahydro-[(1,3)-thioxolane-2,3'-(2,6)-methano-2'H-quinolizin]-8"-yl-2,3-dihydro-3,3-dimethyl-1H-indole-1-carboxamide or a pharmaceutically acceptable salt thereof.

13. The compound of claim 1 wherein the compound is Trans-2,3-Dihydro-3,3-dimethyl-N-(octahydro-3-oxo-2,6-methano-2H-quinolizin-8-yl)1H-indole-1-carboxamide ethane dioate hydrate or a pharmaceutically acceptable salt thereof.

14. The compound of claim 1 wherein the compound is trans-5-chloro-2,3-dihydro-2,2-dimethyl-N-[(octahydrospiro-(1,3-dioxolane-2,3'-(2,6)-methano-2'H-quinolizin)-8'-yl]-7-benzofurancarboxamide or a pharmaceutically acceptable salt thereof.

15. The compound of claim 1 wherein the compound is trans-5-chloro-2,3-dihydro-2,2-dimethyl-N-[octahydro-(3-oxo-2,6-methano-2H-quinolizin)-8-yl]-7-benzofurancarboxamide or a pharmaceutically acceptable salt thereof.

16. A compound of claim 1 wherein the compound is trans-5-chloro-2,3-dihydro-2,2-dimethyl-N-[octahydro-(3-hydroxy-2,6-methano-2H-quinolizin)-8-yl]-7-benzofurancarboxamide or a pharmaceutically acceptable salt thereof.

17. The compound of claim 1 wherein the compound is trans-N-[octahydrospiro(1,3-thioxolane-2,3'-(2,6)-methano-2'H-quinolizin)-8'-yl]-1-benzotriazolecarboxamide or a pharmaceutically acceptable salt thereof.

18. A pharmaceutical composition comprising the compound of claim 1 and a pharmaceutically acceptable carrier.

19. A method of antagonizing the effects of serotonin at the $5HT_3$ receptor to treat a condition responsive to such treatment comprising administering a condition-treating effective amount of the compound of claim 1 to a patient in need of such therapy.

20. The method of claim 19 wherein the condition is chemotherapeutically-induced nausea and vomiting.

21. The method of claim 19 wherein the condition is psychosis.

22. A method of making a compound of the formula (I)

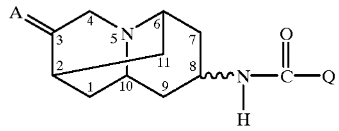

hydrates, tautomers, stereo and geometric isomers, or the pharmaceutically acceptable acid addition or quaternary ammonium salts thereof, wherein A is $H_2$, O, (H)(OH), $NOR_1$, or

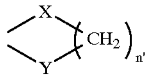

with n being 2 or 3,

X and Y are O or S, each $R_1$ is independently H or $C_{1-4}$ alkyl, $R_2$ is H, halogeno, $C_{1-4}$ alkyl, $C_{1-4}$ alkoxy, $C_3$–$C_6$ cycloalkylmethoxy, OH, —CN or $C(O)NH_2$, Z is O, S or $NR_1$, Q is a heterocyclic or carbocyclic moiety of the formulae (a)

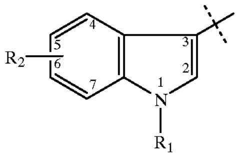

(b)

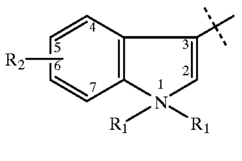

-continued (c)

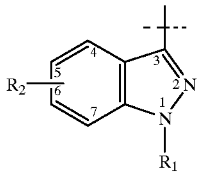

(d)

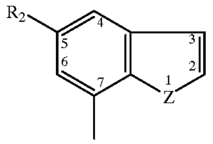

(e)

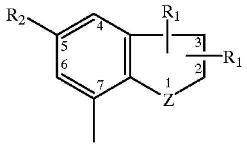

(f)

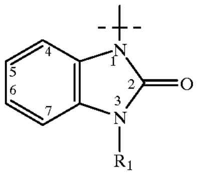

(g)

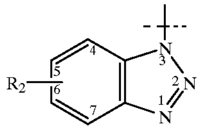

(h)

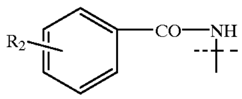

(i)

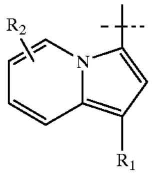

(j)

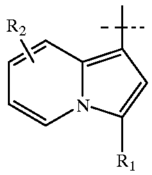

(k)

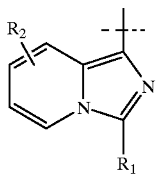

-continued (l)

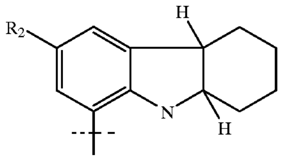

(m)

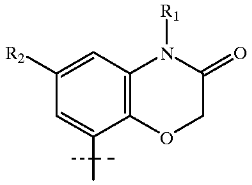

(n)

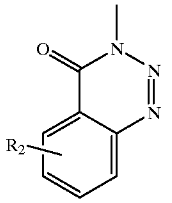

comprising the steps of:

reacting a di-amine or reactive derivation thereof, the diamine having the formula (6)

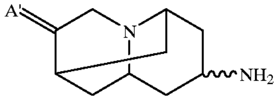

wherein A' is $=H_2$ or $—X—(CH_2)_2—Y—$ or $—X—(CH_2)_3—Y—$ with X and Y being independently O or S, with a reactive equivalent of an acid of the formula

QCOOH

Q being as previously defined;

and optionally protecting appropriate moieties of Q with appropriate protecting groups during the reaction, and, subsequent to the reaction, optionally removing the protecting groups.

23. The method of claim 22 wherein A is $H_2$, O, (H)(OH) or

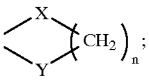

;

$R_2$ is H, halogeno, $C_{1-4}$alkyl or $C_{1-4}$alkoxy; and Q is (a), (b), (c), (d), (e), or (g).

* * * * *

UNITED STATES PATENT AND TRADEMARK OFFICE

CERTIFICATE OF CORRECTION

PATENT NO. : 5,955,470

DATED : September 21, 1999

INVENTOR(s) : Maurice W. Gittos

It is certified that error appears in the above-identified patent and that said Letters Patent is hereby corrected as shown below:

Column 2, Line 5, structure (b) reads as

" 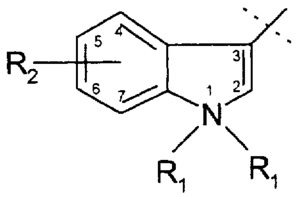 "

and should read as

-- 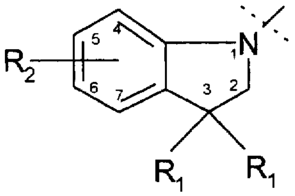 --

Column 3, Line 15, within the structure (l) reads as "N" and should read as --Z--.

Column 3, Line 50 reads as "isomers,and" and should read as --isomers, and--.

UNITED STATES PATENT AND TRADEMARK OFFICE
CERTIFICATE OF CORRECTION

PATENT NO. : 5,955,470

DATED : September 21, 1999

INVENTOR(s) : Maurice W. Gittos

It is certified that error appears in the above-identified patent and that said Letters Patent is hereby corrected as shown below:

Column 4, Line 15, structure (b) reads as

" 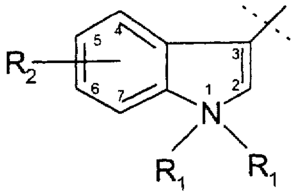 " and should read as

-- 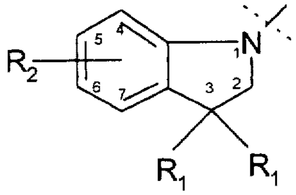 --

UNITED STATES PATENT AND TRADEMARK OFFICE
CERTIFICATE OF CORRECTION

PATENT NO. : 5,955,470

DATED : September 21, 1999

INVENTOR(s) : Maurice W. Gittos

It is certified that error appears in the above-identified patent and that said Letters Patent is hereby corrected as shown below:

Column 14, Line 40, the structure below the caption Example 18 reads as

"

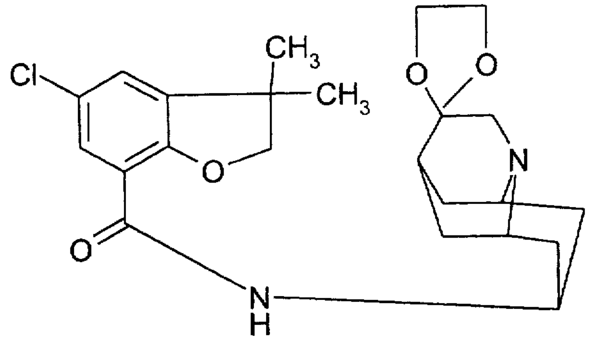

"

and should read as

--

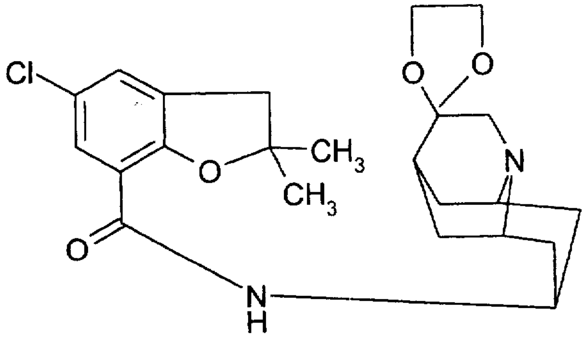

--.

UNITED STATES PATENT AND TRADEMARK OFFICE
CERTIFICATE OF CORRECTION

PATENT NO. : 5,955,470

DATED : September 21, 1999

INVENTOR(s) : Maurice W. Gittos

It is certified that error appears in the above-identified patent and that said Letters Patent is hereby corrected as shown below:

Column 15, Line 5, the structure below the caption Example 19 reads as

" 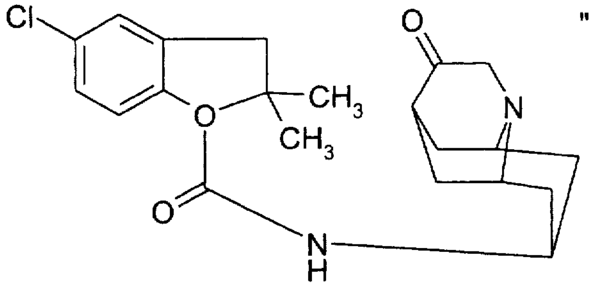 "

and should read as

-- 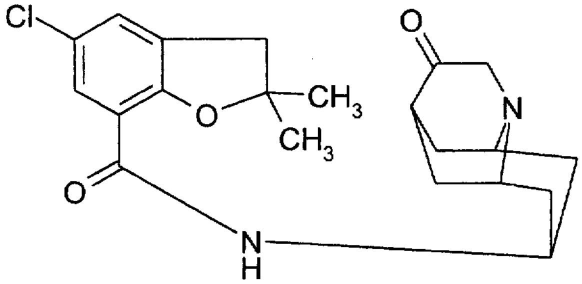 --

UNITED STATES PATENT AND TRADEMARK OFFICE
CERTIFICATE OF CORRECTION

PATENT NO. : 5,955,470

DATED : September 21, 1999

INVENTOR(s) : Maurice W. Gittos

It is certified that error appears in the above-identified patent and that said Letters Patent is hereby corrected as shown below:

Column 15, Line 35, the structure below the caption Example 20 reads as

"

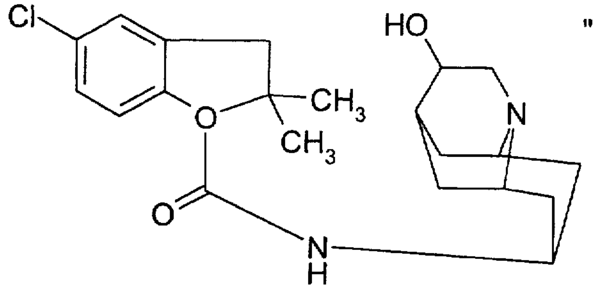

"

and should read as

--

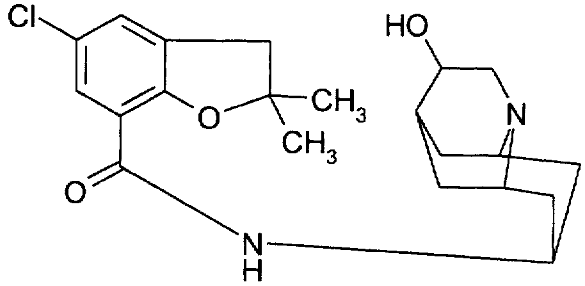

--

Column 19, Lines 14 and 15 read as "and the weighed" and should read as --and then weighed--.

Column 19, Line 15 reads as "stomach" and should read as --stomachs--.

Column 21, Line 27 reads as "accuring" and should read as --occuring--.

UNITED STATES PATENT AND TRADEMARK OFFICE
CERTIFICATE OF CORRECTION

PATENT NO. : 5,955,470

DATED : September 21, 1999

INVENTOR(s) : Maurice W. Gittos

It is certified that error appears in the above-identified patent and that said Letters Patent is hereby corrected as shown below:

Column 23, Line 16 reads as "sweeting" and should read as --sweetening--.

Column 24, Line 30 reads as "race" and should read as --rate--.
Column 25, Line 55, structure (b) reads as " 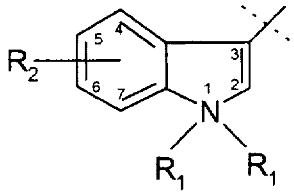 "

and should read as

-- 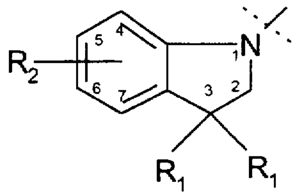 --

Column 26, Line 60, within the structure (I) reads as "N" and should read as --Z--.

UNITED STATES PATENT AND TRADEMARK OFFICE
CERTIFICATE OF CORRECTION

PATENT NO. : 5,955,470

DATED : September 21, 1999

INVENTOR(s) : Maurice W. Gittos

It is certified that error appears in the above-identified patent and that said Letters Patent is hereby corrected as shown below:

Column 28, Line 65, structure (b) reads as

" 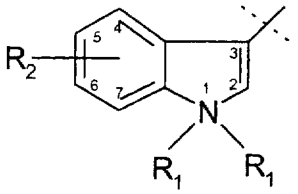 "

and should read as

-- 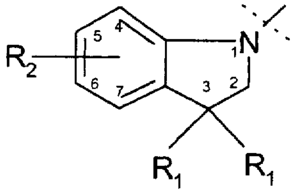 --

Column 30, Line 5, within the structure (l) reads as "N" and should read as --Z--.

Signed and Sealed this

Seventeenth Day of April, 2001

Attest:

NICHOLAS P. GODICI

Attesting Officer

*Acting Director of the United States Patent and Trademark Office*